United States Patent [19]

Limon

[11] Patent Number: 4,876,904

[45] Date of Patent: Oct. 31, 1989

[54] METHOD AND AUTOMATIC DEVICE FOR MEASURING THE CONTENT OF A SOLUBLE COMPONENT IN A POWDERY PRODUCT

[75] Inventor: Bernard Limon, Ceyzeriat, France

[73] Assignee: Hasler Freres International S.A., Switzerland

[21] Appl. No.: 44,845

[22] PCT Filed: Jul. 14, 1986

[86] PCT No.: PCT/CH86/00097
§ 371 Date: Apr. 16, 1987
§ 102(e) Date: Apr. 16, 1987

[87] PCT Pub. No.: WO87/00636
PCT Pub. Date: Jan. 29, 1987

[30] Foreign Application Priority Data

Jul. 16, 1985 [FR] France ................. 85 10987

[51] Int. Cl.⁴ ............ G01N 33/38; G01N 27/00; G01N 5/00
[52] U.S. Cl. ........................... 73/866; 73/61 R; 430/150; 430/178
[58] Field of Search ............ 73/866, 61 R; 436/150, 436/178; 324/62, 65 R; 177/50

[56] References Cited

U.S. PATENT DOCUMENTS

| | | |
|---|---|---|
| 3,870,465 | 3/1975 | Maréchal . |
| 4,391,774 | 7/1973 | Dupain .............. 141/103 X |
| 4,726,896 | 2/1988 | Grove et al. .......... 73/61 R X |
| 4,753,889 | 6/1988 | Collins .............. 436/178 X |

FOREIGN PATENT DOCUMENTS 2485733 12/1981 France .
2564592 11/1985 France .

*Primary Examiner*—Tom Noland
*Attorney, Agent, or Firm*—Lerner, David, Littenberg, Krumholz & Mentlik

[57] ABSTRACT

A method for automatically determining the quantity of a soluble component in a powdery product is disclosed comprising providing a sample receiving container, weighing the sample receiving container, computing the weight of a predetermined quantity of solvent for the soluble component and introducing that predetermined quantity of solvent to the sample receiving container, introducing a predetermined quantity of the powdery product into the sample receiving container including the computed weight of solvent, weighing the solvent containing container with the predetermined quantity of powdery product and solvent therein, computing the weight of the predetermined quantity of powdery product, computing the weight ratio of the predetermined quantity of powdery product to the predetermined quantity of solvent, agitating the predetermined quantity of powdery product and solvent within the sample receiving container so as to create a solution thereof, determining an electrical characteristic of the solution, and correcting the electrical characteristic of the solution as a function of the weight ratio of the predetermined quantity of powdery product to the predetermined quantity of solvent therein.

9 Claims, 2 Drawing Sheets

METHOD AND AUTOMATIC DEVICE FOR MEASURING THE CONTENT OF A SOLUBLE COMPONENT IN A POWDERY PRODUCT

BACKGROUND OF THE INVENTION

The present invention relates to a method of measuring the lime content of a powdery product, comprising the steps of introducing a determined quantity of the powdery product and a determined quantity of a solvent into a recipient, agitating this mixture so as to dissolve the lime in the solvent, and measuring in this mixture an electrical characteristic representing said lime content.

The invention also relates to a device for measuring the content of a soluble component in a powdery product, comprising at least one recipient, means for dosing a given quantity of a solvent and bringing it to said recipient, means for dosing a given quantity of the powdery product and bringing it to the recipient, means for agitating the contents of the recipient, means for measuring an electrical characteristic in the contents of the recipient, and means for discharging the contents of the recipient after this measurement.

The invention applies particularly, but not exclusively, to the measurement of the free lime content of cement or cement clinker.

In cement works such a measurement is regularly made on a sample of clinker taken from the kiln exit, then cooled and crushed, with the object of controlling the production, especially the burning process in the kiln.

French Pat. No. 2 163 963 describes a method and a device for carrying out this measurement in a manner allowing automatic operation of a cement plant kiln. One uses in this case a device comprising on one hand a chamber, in which a mixture of the crushed clinker sample and heated glycol is prepared and an electrical characteristic of this mixture is measured, and on the other hand means for supplying dosed volumes of clinker and glycol to this compartment. The dosing and supply means for the crushed clinker are described in more detail in French Pat. No. 2 182 283 and comprise a calibrated assay crucible, into which the clinker is poured and packed, then levelled to constitute the desired volume. This crucible is next brought mechanically by a mobile arm above the chamber to empty the clinker into it.

This operating mode and this device still have various drawbacks which affect the precision of the measurement and the reliability of the process, and hence also the quality of the clinker produced in the kiln in the case of automatic operation. First of all the density of the crushed clinker sample may vary, in particular with the granulometry of the sample. This occurs especially in the case of malfunction of the kiln, producing an "unburnt" clinker whose grindability differs from that of normal clinker. As a result, the quantity of clinker introduced into the measuring chamber also varies and the measurement is given an erroneous value. Now, it is precisely in such a case that the production has to be corrected.

On the other hand, the volumetric determination of the quantities with this device does not allow for control in an automatic process. If one of the supply devices malfunctions, the measurement may be effected on false quantities, for example if the calibrated assay crucible is not completely filled with clinker before levelling. The same applies in the case of malfunction of the pump for glycol.

In addition, the measuring chamber is a complex and delicate instrument. In particular, its complete evacuation between two operating cycles is not always ensured, because the valves may be obstructed. The displacement of the mobile electrode which it contains is also subject to faulty operation.

Consequently, the present invention has the object of meeting these drawbacks, by providing a method of the type mentioned in the preamble and allowing precise and reliable measurement of the lime content to be achieved, by means of a device including relatively simple and proven components. The invention shall particularly ensure highly reliable operation of the successive measurements carried out during automatic operating cycles of the device, in order to be fit for use in an automatic system for controlling the production of the powdery product.

SUMMARY OF THE INVENTION

To this end, the measuring method according to the invention is characterized in that the weight of the powdery product introduced into the recipient is measured, by weighing the recipient before and after introduction of this product, in that the weight ratio between the respective quantities of the powdery product and the solvent introduced into the recipient is calculated, and in that the result of said measurement of an electrical characteristic is corrected as a function of this ratio.

The weight of said quantity of solvent is preferably also measured by weighing the recipient before and after introducing the solvent.

According to a preferred embodiment of the method, wherein automatic measuring cycles controlled by an electronic calculator are carried out, this calculator receives signals representing weighings, it calculates the respective weights of the product and the solvent, as well as said weight ratio, and it corrects said measurement of an electrical characteristic in such a manner as to deliver at least one output signal representing the lime content of the powdery product. This output signal is especially suitable for displaying the results of the measurement and/or the automatic operation of the plant for manufacturing the powdery product.

With this preferred mode of the method, at least one calibration of the weighing means may be carried out during the automatic measuring cycle, while the calculator corrects the results of the weighings in accordance with the calibration. On the other hand, the calculator may automatically modify a measuring cycle if one of the measured or calculated weights lies outside a corresponding predetermined range.

The device according to the invention is adapted to allow this method to be carried out and is characterized in that it includes means for displacing the recipient and means for weighing it.

According to a preferred embodiment of the device, the means for displacing the recipient comprise a clamp adapted to grip the recipient and mounted on a motorized support arranged for displacing the recipient along a horizontal arc of a circle, for vertical translation and for pivoting round a substantially horizontal axis.

The means for weighing the recipient preferably include an electronic balance. According to another variant, these means include a sensor with a strain gauge.

The means for dosing a given quantity of the solvent preferably include a positive displacement pump. The means for dosing a given quantity of the powdery product likewise include volumetric dosing means. These volumetric dosing means need not ensure extremely precise dosing; they may especially consist of a rotary plate equipped with a scraper.

The present invention and its advantages will be better understood by the description of an embodiment, provided for dosing the free lime in a sample of cement clinker, after crushing this sample. This description is given below by way of a non-limiting example, with reference to the accompanying drawings, wherein:

DESCRIPTION OF THE PREFERRED EMBODIMENT

Figure 1:
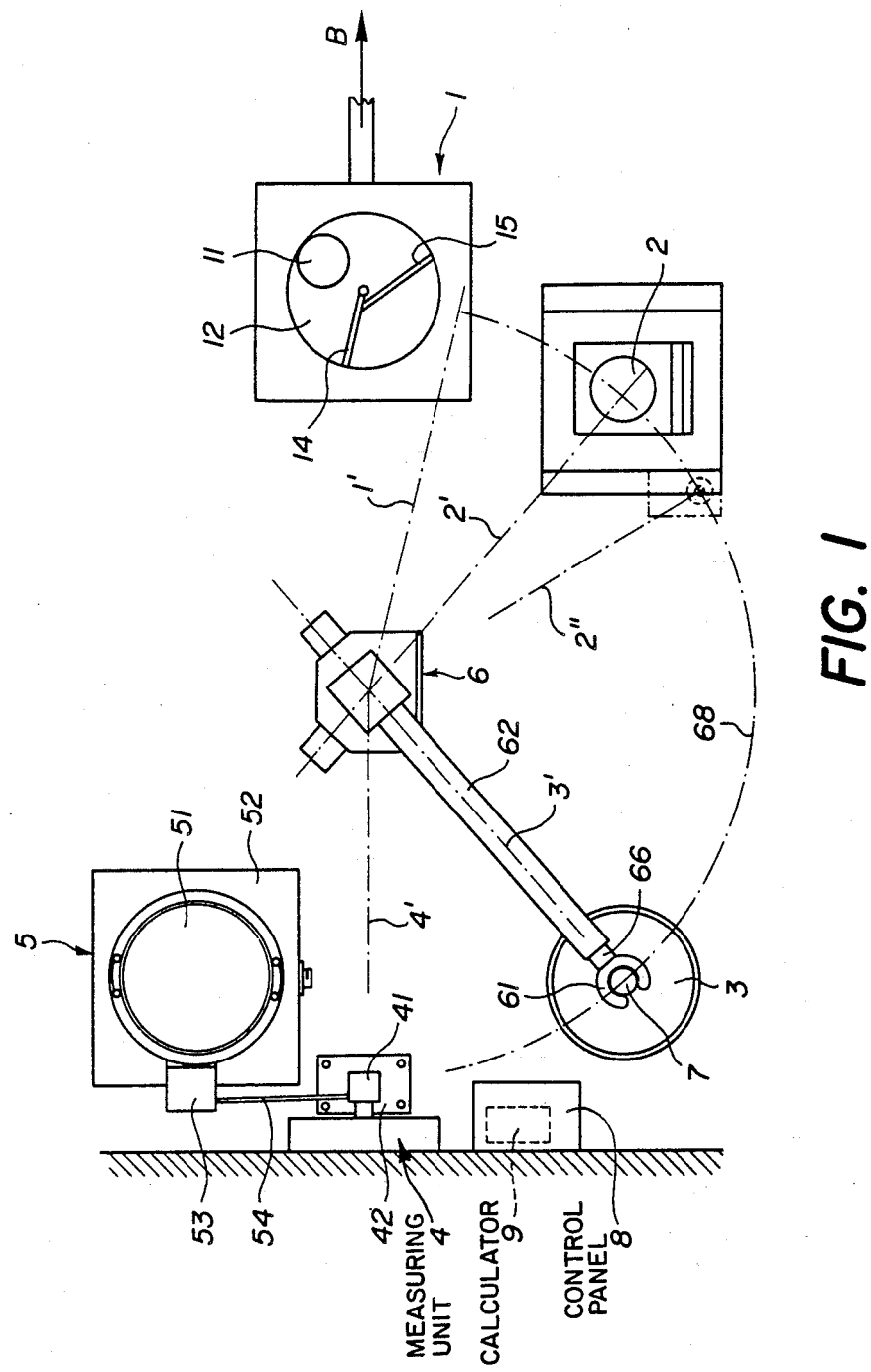
FIG. 1 is a schematic plan view of the device according to the invention.
Figure 2:
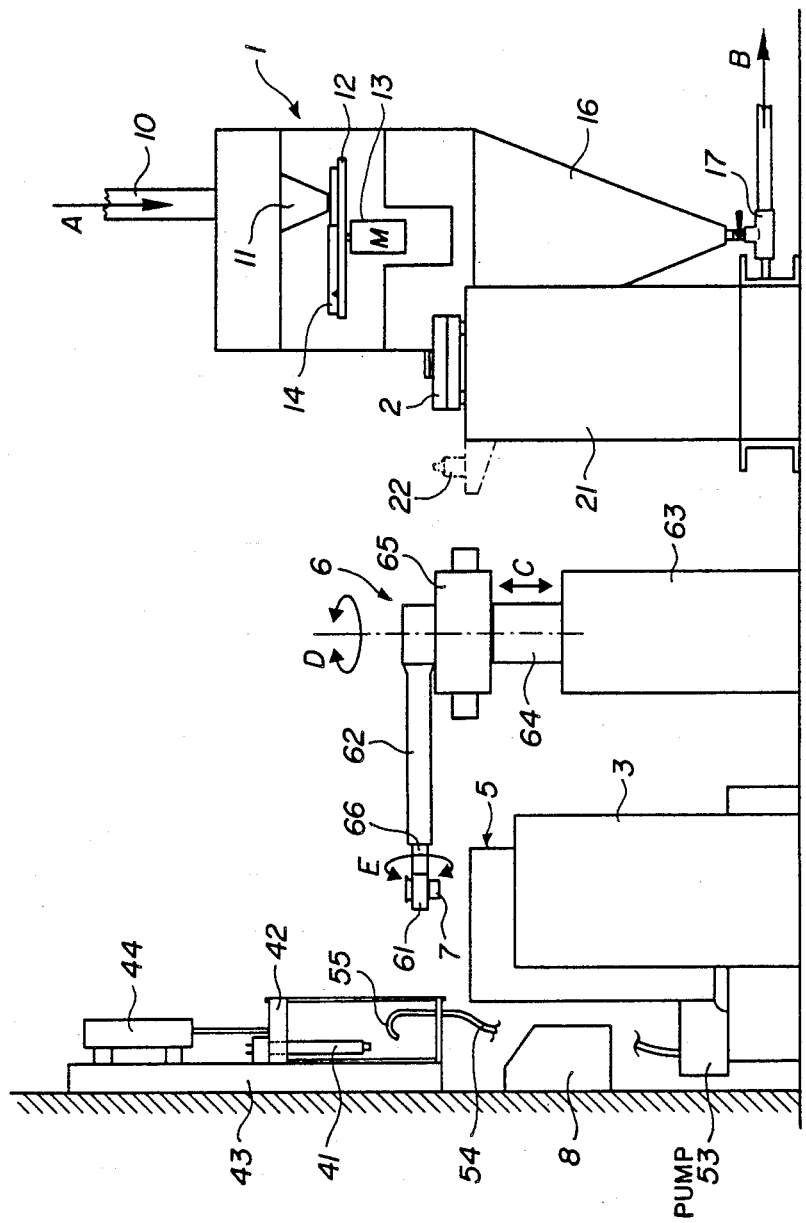
FIG. 2 is a schematic elevational view of the device represented in FIG. 1.

With reference to the figures, the device represented essentially includes a distributor 1 for the crushed clinker, an electronic balance 2, an evacuating tank 3, a measuring unit 4, a glycol supply unit 5 and a manipulating robot 6 for displacing a measuring recipient 7. In this case the recipient 7 is a conventional beaker, but it may evidently consist of any type of recipient open at the top and appropriate for its function. The device further comprises a control panel 8 equipped with a calculator 9.

The distributor 1 is connected to the outlet of a clinker supply pipe 10, through which the clinker samples taken from the exit of the kiln, then cooled and crushed, arrive in the direction of the arrow A, to a hopper 11. Under this hopper lies a rotary plate 12 driven intermittently by a motor 13. A scraper consisting of two elements 14 and 15 is disposed in a fixed position above the upper face of the plate 12. The first element 14 includes a hole or a notch for forming on the plate a band of clinker of determined volume, while the second element 15 is disposed obliquely in such a manner as to push this band out of the plate 12 and to tip into the recipient 7 brought below it. The excess material situated in front of the element 14 falls into a discharge hopper 16, from which it is periodically evacuated in the direction of the arrow B by means of an ejector 17.

The balance 2 is an electronic precision balance, with a range of 100 to 200 grams and a step of 1 mg. It is mounted at an appropriate height on a support 21 and is electrically connected to a calculator 9 to transmit thereto the results of each weighing.

As a variant, the balance 2 may be replaced by a sensor with a strain gauage, which must then be automatically recalibrated at each measuring cycle, by depositing a standard weight 22 represented in dashed lines in the drawing.

The evacuating tank 3 is open at the top, so that the contents of the recipient may be easily emptied into it. This tank is only represented schematically; it may consist for example of a simple barrel which is open at the top and is periodically replaced, or by a more intricate reservoir equipped with filters and with an extraction pump for recycling the glycol.

The glycol supply unit 5 is disposed near to the measuring unit 4. In the example illustrated here, it compares a glycol reservoir 51, mounted on a heating device 52 controlled by a thermostat, and a positive displacement pump 53, for example a peristaltic pump, which is connected to the measuring unit 4 by a glycol distributing pipe 54. In the measuring unit, the end of the pipe 54 is provided with a spout 55 for pouring the warm glycol into the recipient 7.

The measuring unit 4 includes a set of instruments 41 intended to be plunged into the contents of the recipient 7 during the process. For this purpose, the set of instruments 41 is mounted on a chassis 42 which is vertically mobile along a wall support 43, by means of a small jack 44 which may be for example an electric jack.

The set of instruments 41 is only represented schematically, because it simply combines several instruments each of which is well known. These are in this case an agitator for mixing the glycol and the powder clinker in the recipient 7, a temperature regulator comprising a heat sensor and a heating element, for maintaining the mixture at a precise temperature and communicating this temperature to the control means, and a pair of electrodes adapted to provide the electrical measurement, which is preferably a measurement of the conductivity of the mixture, but which may also be a measurement of a potential, of the pH or of a similar characteristic.

As will be described below, the recipient 7 must be displaced several times between the devices 1 to 4 during a measuring cycle. To this end, it is carried by a clamp 61 disposed at the end of a horizontal arm 62 of a manipulating robot 6. This consists of an apparatus with three degrees of displacement, of a type well known in material handling engineering and essentially including a fixed base 63, a vertical column 64 vertically mobile with respect to the base, in the direction of the double arrow C, and the arm 62 mounted at the top of the column 64 so as to swivel round the vertical axis of this column, according to the arrow D and through the action of a mechanism 65. The free end 66 of the arm 62 carries the clamp 61 and is adapted to swivel around the horizontal axis of this arm, in the direction of the double arrow E. A mechanism for opening and closing the clamp 61 is accomodated in the arm 62. As is shown in FIG. 1, the manipulating robot 6 is installed at the center of an arc of a circle 68 along which the elements 1 to 4 of the device are distributed. In plan view, displacements of the recipient 7 all take place along this arc of a circle. In FIG. 1, the respective positions of the recipient 7 near to the different apparatuses 1 to 4 are indicated by the corresponding positions of the axis of the arm 62, indicated by the references 1', 2', 3' and 4. Another position 2" is indicated for the case where the standard weight 22 is used.

With the method according to the present invention, an operating cycle of the device described above takes place as follows, while all operations of this cycle are automatically controlled and checked from the control panel 8. At rest, the recipient 7 is filled with glycol and lies in the position 3' above the evacuating tank 3.

By pivoting the end 66 of the arm, the recipient is turned upside down and emptied into this tank, and next brought into the position 2" to be deposited on the balance 2 and to be calibrated. The balance transmits the tare weight of the recipient 7 to the calculator 9. The manipulator 6 next grasps the recipient 7 once more by the clamp 61 and brings in into the position 4' for it to receive a dose of hot glycol, for example 50 ml, delivered by the peristaltic pump 53 and the pipe 54. The recipient is then brought back to the position 2" to be weighed on the balance, while the calculator 9 then calculates the exact weight of the glycol dose by the difference between the weight of the recipient before and after introduction of the glycol.

The recipient is then brought to the position 1' and the rotary plate 12 of the distributor 1 is brought into action for a duration corresponding to pouring out a given volume of powdery clinker into the recipient, this volume being determined so as to correspond approximately to one gram of clinker. To determine the exact weight of the quantity of clinker introduced into the recipient, the latter is weighed once more on the balance 2, while the calculator 9 again determines this weight by the difference between the weighings before and after. The calculator 9 also calculates the ratio between the weight of the glycol and the weight of the clinker. The recipient 7 is brought back into the position 4' for the conductivity measurement. The set of instruments 41 is lowered by the jack 44 down to the recipient, then the temperature regulator is made to operate and the agitator is actuated for a determined duration. Next, if the temperature lies in the required range, the conductivity measurement is effected and transmitted to the calculator 9, which corrects it as a function of the weight ratio of the clinker and the glycol and delivers a preferably numerical output signal, for display of the results on the panel 8 and for the control means of the kiln in which the clinker is produced. The set of instruments 41 is then raised again and the recipient 7 is brought back into the position 3' to empty its contents into the tank 3 in view of recycling the glycol. The recipient is then rinsed, while receiving in the position 4' a new dose of glycol, which may possibly be stirred by the agitator and which is then poured out into the tank 3, the recipient 7 then remaining in the rest position at 3'.

In the case where the electronic balance 2 is replaced by a sensor with a strain gauge, the operating cycle further includes at least one phase for calibrating this sensor, during which the recipient 7 is deposited by the clamp 61 in a stand-by position 1', while this clamp is used to seize the standard weight 22 in the position 2", to bring it into the position 2' to be weighed, then setting it back in place.

The calculator 9 then determines the weight of the recipient as a function of the weight indicated by the sensor for the standard 22.

With the method described above, as all results are transmitted to the calculator 9 the latter may effect tests on these results and interrupt or recommence the cycle if one of the values goes beyond the predetermined range of tolerance.

One thus avoid the risks inherent in volumetric dosage according to the prior art, with which an insufficiency or an excess of one or the other of the components went undetected.

This method allows complete freedom from the error in sampling of which the weight is known with precision. The measurement may moreover be made repeatedly without taking particular precautions that the weight of the substances taken up in each sampling remain within predetermined limits.

A system in which the samples whose weight is too far away from a determined value, fixed by the operator, are removed, is described in French Pat. No. 2,564,592. The drawback of such a system resides in the fact that several samples may possibly be rejected successively, for example if the recipient used for collecting them is only incompletely filled due to any defect of the control means. The rejection of several successive samples entails a loss of measurements which may lead to faults in production, given that the measurements are exploited to ensure the automatic control of production.

Moreover, in the device described above, one only uses relatively simple means which are to a small extent subject to disturbance. In addition, these means are easily adapted to the installation of operational control means, for example sensors detecting the presence or absence or the position of the recipient 7, as well as the quantities of clinker or glycol still available. One thus obtains a very great operating safety and excellent reliability of the measurement results.

Tests have shown that, in a cement plant, a device according to the invention is capable of carrying out a cycle every ten minutes, hence correcting burning of the clinker in the kiln practically in real time.

The present invention is not limited to the embodiment described above by way of example, but it extends to any modification or variant obvious to one skilled in the art. In particular, the device is not limited to the measurement of the lime content in cement clinker, but it is fit for use, with the appropriate modifications for the particular case, for any measurement of the content of a soluble component, in a powdery product.

I claim:

1. An automatic method of determining the quantity of a soluble component in a powdery product comprising the steps of:
    (a) providing a sample receiving container;
    (b) weighing said sample receiving container;
    (c) computing the weight of a predetermined quantity of a solvent for said soluble component and introducing said predetermined quantity of solvent into said sample receiving container;
    (d) introducing a predetermined quantity of said powdery product into said sample receiving container including said computed weight of said solvent;
    (e) weighing said solvent receiving container with said predetermined quantity of said powdery product and said solvent therein;
    (f) computing the weight of said predetermined quantity of said powdery product;
    (g) computing the weight ratio of said predetermined quantity of said powdery product to said predetermined quantity of said solvent;
    (h) agitating said predetermined quantity of said powdery product and said predetermined quantity of said solvent within said sample receiving container so as to create a solution of said soluble component in said powdery product;
    (i) determining an electrical characteristic of said solution of said soluble component in said powdery product; and
    (j) correcting said electrical characteristic of said solution as a function of said weight ratio of said predetermined quantity of said powdery product to said predetermined quantity of said solvent.

2. The method according to claim 1, wherein said step (c) comprises individually introducing said predetermined quantity of said solvent into said sample receiving container, weighing said sample receiving container with said predetermined quantity of said solvent therein, and computing the weight of said predetermined quantity of said solvent.

3. The method according to claim 1, wherein said solvent comprises a glycol, and wherein said predetermined characteristic comprises conductivity.

4. The method according to claim 3 including the step of terminating said method if said weight of said sample receiving container as determined in step (b), or said weight of said predetermined quantity of said solvent as determined in step (c), or said weight of said predetermined quantity of said powdery product as determined in step (f), are beyond a predetermined acceptability range.

5. The method according to claim 3 including the step of maintaining said glycol within a predetermined temperature range; and terminating said method if the temperature of said glycol is not within said predetermined temperature range.

6. The method according to claim 1, further including the steps of automatically repeating steps (a) through (j) at predetermined time intervals.

7. The method according to claim 1 including the additional steps of:
(k) emptying said sample receiving container after step (j); and
(l) rinsing said sample receiving container.

8. The method of claim 7 wherein said step (l) includes refilling said sample receiving container with solvent, agitating said sample receiving container and emptying said sample receiving container.

9. The method according to claim 8 including recycling said solvent for continued use.

* * * * *